United States Patent [19]
Williams et al.

[11] Patent Number: 5,447,928
[45] Date of Patent: Sep. 5, 1995

[54] BENZOXAZINE DERIVATIVES AND THEIR APPLICATION IN THERAPY

[75] Inventors: Howard Williams, Paris; Lydia Zard, Gif sur Yvette; Thomas Purcell, Montfort l'Amaury; Daniel Galtier, Guyancourt; Jean-Claude Muller, Morsang sur Orge; Pascal George, St Arnoult en Yvelines; Jonathan Frost, Wissous; Patrick Pasau, Bagneux; Corinne Rousselle, Fontenay aux Roses; Régine Bartsch, Bischheim, all of France

[73] Assignee: Synthelabo, Le Plessis Robinson, France

[21] Appl. No.: 201,233

[22] Filed: Feb. 24, 1994

[30] Foreign Application Priority Data

Mar. 8, 1993 [FR]   France ................. 93 02659

[51] Int. Cl.$^6$ ................. A61K 31/535; C07D 265/36; C07D 413/06
[52] U.S. Cl. ................. 514/213; 514/230.5; 544/105; 540/594
[58] Field of Search ................. 540/594; 544/105; 514/213, 230.5

[56] References Cited

PUBLICATIONS

*Cecil Textbook of Medicine*, 19th edition (1992) Wyngaarden, M.D. editor, pp. 2075–2078.
Techer, H., "Tetrahydro–1,2,3,3a 4H–pyrrolo–(2.1–c) benzoxazine–1,4 et Derivatives", Comptes Rendus des Seances de L'Academie des Sciences, Serie C., vol. 274, No. 11, 1972, pp. 1081–1083.

*Primary Examiner*—Philip I. Datlow
*Attorney, Agent, or Firm*—Jacobson, Price, Holman & Stern

[57] ABSTRACT

Compounds of the formula

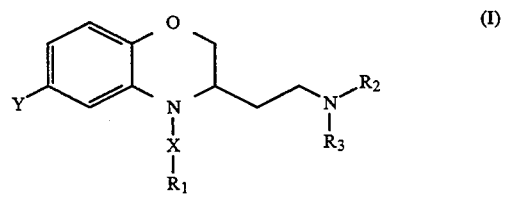

in which Y represents hydrogen, fluorine, chlorine, methyl or methoxy, $R_1$ represents phenyl substituted by fluorine, methyl, methoxy, trifluoromethyl or phenyl, or $R_1$ represents 2-thienyl, $R_2$ represents methyl, and $R_3$ represents $(C_1-C_4)$-alkyl, or phenyl-$(C_1-C_2)$-alkyl optionally substituted on the ring by 2 to 3 methoxy groups, or 2-(2-pyridyl)ethyl, or $R_2$ and $R_3$ form, with the adjacent nitrogen, 4-phenyl(1-piperidyl), 4-phenylmethyl(1-piperidyl), 1,2,3,4-tetrahydro-2-isoquinolyl, 6-methoxy-1,2,3,4-tetrahydro-2-isoquinolyl, 5,8-dimethoxy-1,2,3,4-tetrahydro-2-isoquinolyl, 6,7-dimethoxy 1,2,3,4-tetrahydro-2-isoquinolyl, 2,3,4,5-tetrahydro-1H-3-benzazepin-3-yl, or 7,8-dimethoxy-2,3,4,5-tetrahydro-1H-3-benzazepin-3-yl, and X represents carbonyl or sulphonyl, and their salts are useful as neuroprotective and antiiischaemic agents.

4 Claims, No Drawings

BENZOXAZINE DERIVATIVES AND THEIR APPLICATION IN THERAPY

The present invention relates to benzoxazine derivatives, their preparation and their use in therapy.

The compounds of the invention correspond to the formula (I)

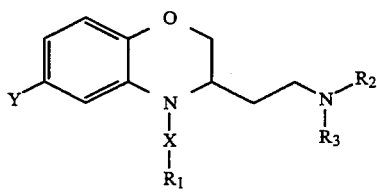

in which
- Y represents hydrogen, fluorine, chlorine, methyl or methoxy,
- $R_1$ represents phenyl substituted by fluorine, methyl, methoxy, trifluoromethyl or phenyl, or $R_1$ represents a 2-thienyl group,
- $R_2$ represents methyl, and
- $R_3$ either represents $(C_1-C_4)$-alkyl, phenyl-$(C_1-C_2)$-alkyl which is optionally substituted on the ring by 2 to 3 methoxy groups, or 2-(2-pyridyl)ethyl, or
- $R_2$ and $R_3$ together form, with the nitrogen to which they are attached, 4-phenyl(1-piperidyl), 4-phenylmethyl(1-piperidyl), 1,2,3,4-tetrahydro-2-isoquinolyl, 6-methoxy-1,2,3,4-tetrahydro-2-isoquinolyl, 5,8-dimethoxy-1,2,3,4-tetrahydro-2-isoquinolyl, 6,7-dimethoxy-1,2,3,4-tetrahydro-2-isoquinolyl, 2,3,4,5-tetrahydro-1H-3-benzazepin-3-yl or 7,8-dimethoxy-2,3,4,5-tetrahydro-1H-3-benzazepin-3-yl, and
- X represents carbonyl or sulphonyl, and their salts with pharmaceutically acceptable acids.

Preferred compounds are those of formula (I), in which
- $R_1$ represents a phenyl group which is substituted at position 3 by a trifluoromethyl group, $R_2$ and $R_3$ form, with the adjacent nitrogen, a 6,7-dimethoxy-1,2,3,4-tetrahydro-2-isoquinolyl group, and
- X represents a carbonyl group.

Since the molecule represented by the general formula (I) possesses an asymmetric carbon atom, the compounds of the invention can exist in the form of pure enantiomers or a mixture of enantiomers. The compounds of the invention exist in the form of free bases or of addition salts with pharmaceutically acceptable acids.

These various forms are part of the invention.

In accordance with a feature of the invention, the compounds in which X represents a carbonyl group are prepared according to scheme 1 below.

A 2-aminophenol of formula (II) in which Y is as defined above is reacted with trifluoroacetic anhydride of formula (III), in the presence of a base such as pyridine, in a solvent such as ether. An amide of formula (IV) is obtained which is reacted with ethyl 4-bromobut-2-enoate of formula (V) in the presence of a base such as sodium methoxide, in a solvent such as ethanol, at a temperature in the order of 80° C. The ester functional group of the ethyl 3,4-dihydro-2H-1,4-benzoxazine-3-acetate derivative of formula (VI) is then reduced with a reducing agent such as lithium aluminium hydride, in order to obtain the 3,4-dihydro-2H-1,4-benzoxazine-3-ethanol derivative of formula (VII) which is reacted, in a solvent such as dichloromethane, with an acid chloride of formula (VIII), in which $R_1$ is as defined above, in order to obtain an alcohol of formula (IX), which is reacted with thionyl chloride in order to obtain a compound of formula (X). Finally, the latter compound is reacted with an amine of formula (XI), in which $R_2$ and $R_3$ are as defined above, in order to obtain a compound of formula (Ia), which corresponds to the formula (I) in which X represents a carbonyl group.

Scheme 1

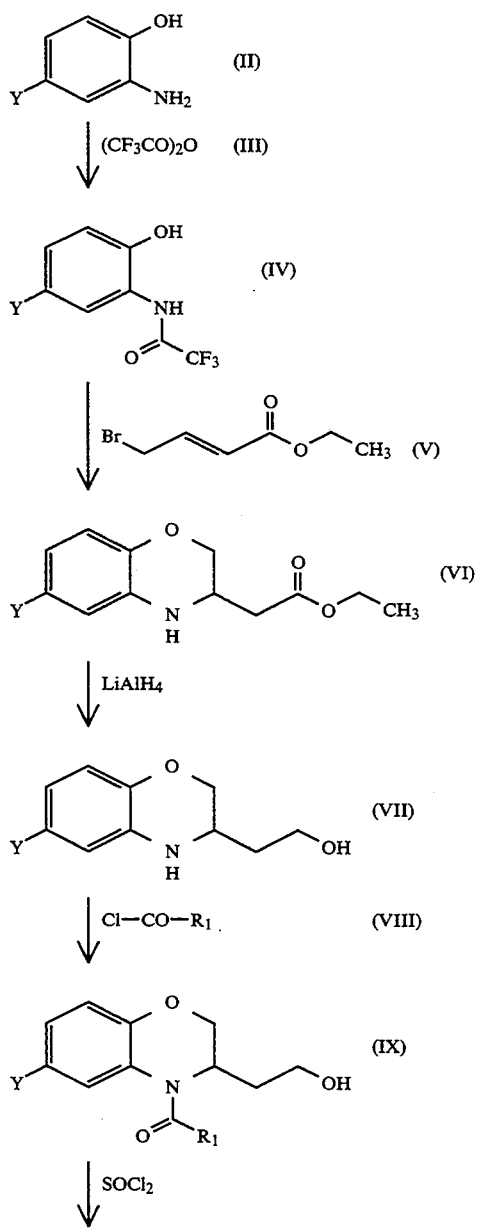

-continued
Scheme 1

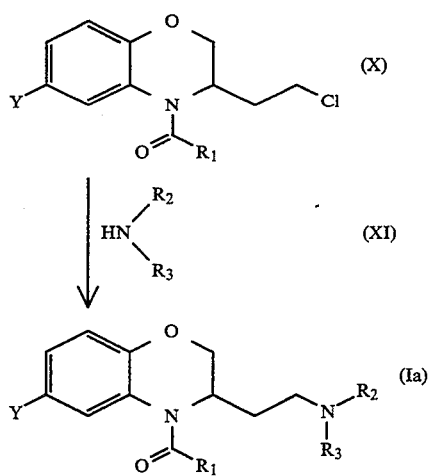

When X represents a sulphonyl group, the compounds of general formula (I) are prepared according to a further feature of the invention according to the following scheme 2.

Scheme 2

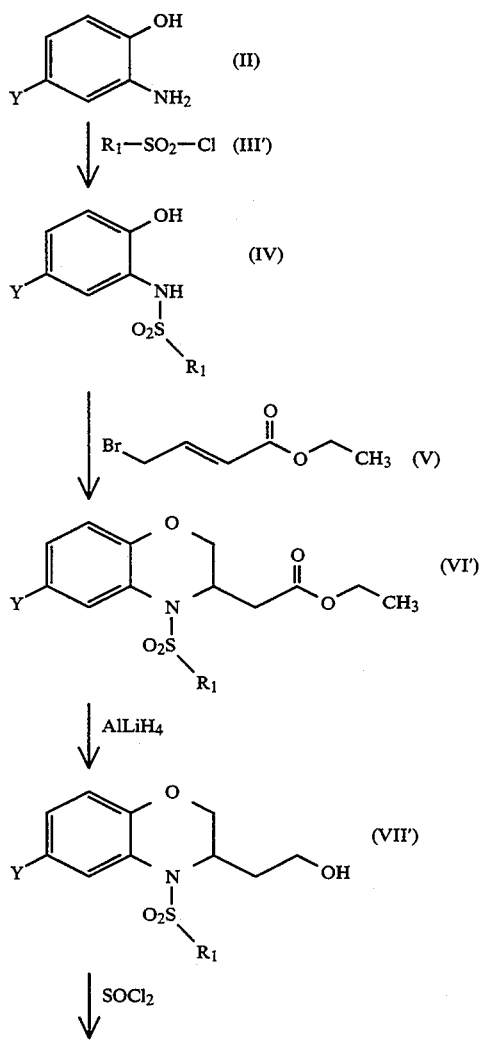

-continued
Scheme 2

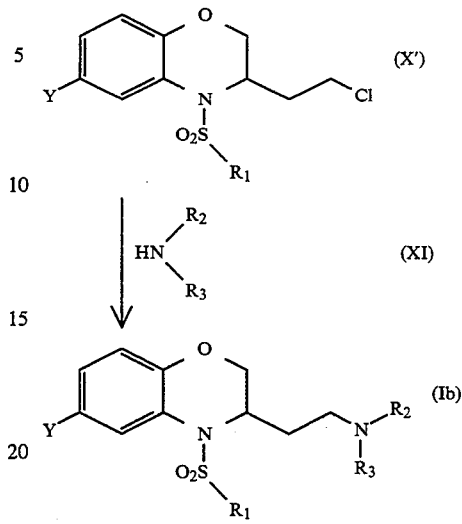

A 2-aminophenol of formula (II) in which Y is as defined above is reacted with a chloride of formula (III') in the presence of a base such as pyridine. A compound of formula (IV') is obtained which is reacted with ethyl 4-bromobut-2-enoate of formula (V) in the presence of a base such as sodium methoxide, in a solvent such as ethanol, at a temperature of 80° C. The ester functional group of the compound of formula (VI') is then reduced with a reducing agent such as lithium aluminium hydride in order to obtain the compound of formula (VII') which is reacted with thionyl chloride, in a solvent such as chloroform, in order to obtain the compound of formula (X') which is finally condensed with an amine of formula (XI) in which $R_2$ and $R_3$ are as defined above.

The starting compounds are commercially available or are described in the literature, or can be synthesized in accordance with methods which are described therein or which are known to the person skilled in the art. In particular, 2-amino-4-methoxyphenol is described in *J.Am. Chem. Soc* (1949) 71 1265.

If it is desired to obtain a compound of formula (I) which is optically pure, it is possible to use an alcohol of formula (IX) or (VII') which is optically pure, which will have been isolated, for example, by an enzymatic method.

The basic principle of this enzymatic method consists in separating an optically pure alcohol from the corresponding acetate of opposite configuration, for example by chromatography on a silica gel column.

According to a first variant, the racemic alcohol of formula (IX) or (VII') is subjected to chemical acylation, for example using acetic anhydride, one of the two enantiomers of the racemic acetate is hydrolysed stereospecifically, in the presence of an enzyme, and the acetate which has not been hydrolysed is separated. An optically pure alcohol is obtained, as is an optically pure acetate of opposite configuration which may, if desired, be itself hydrolysed by a chemical or enzymatic route in order to yield the second enantiomer of the alcohol.

According to a second variant the racemic alcohol of formula (IX) or (VII') is subjected to stereospecific acylation in the presence of an enzyme which catalyses the esterification of one of the enantiomers, for example using vinyl acetate. As previously, an optically pure alcohol is obtained, as is an optically pure acetate of opposite configuration which may, if desired, be itself hydrolysed by a chemical or enzymatic route in order to yield the second enantiomer of the alcohol.

In the two variants it is possible, according to the enzyme used, to obtain the laevorotatory or dextrorotatory enantiomer of the alcohol (IX) or (VII') and its acetate of opposite configuration. The enzymes which can be used are, for example, the lipases from *Mucor miehei*, from *Penicillium cyclopium* or from wheatgerm.

The intermediate compounds are new and are likewise part of the invention. They correspond to the general formula (XII)

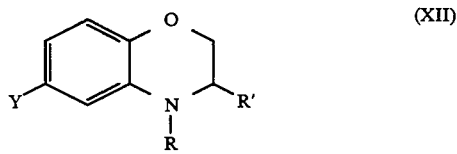

in which Y is as defined above and either R represents a hydrogen atom and R' represents a 2-hydroxyethyl group or R represents a group —$COR_1$ in which $R_1$ is a phenyl group which is substituted by a fluorine atom or by a methyl, methoxy, trifluoromethyl or phenyl group, or is a 2-thienyl group, and R' represents a 2-hydroxyethyl group or a 2-chloroethyl group, or R represents a group —$SO_2R_1$ in which $R_1$ is a phenyl group which is substituted by a fluorine atom or by a methyl, methoxy, trifluoromethyl or phenyl group, or a 2-thienyl group, and R' represents a 2-hydroxyethyl group or a 2-chloroethyl group or an ethoxycarbonylmethyl group.

The following Examples illustrate in detail the preparation of some compounds according to the invention. The elemental microanalyses and the IR and NMR spectra confirm the structures of the products obtained.

The numbers given in brackets in the titles of the examples correspond to those of the table which is given subsequently.

EXAMPLE 1

(Compound No. 28)

(±)-3-[2-(7,8-Dimethoxy-2,3,4,5-tetrahydro-1H-3-benzazepin-3-yl)ethyl]-4-[3-(trifluoromethyl)benzoyl]-3,4-dihydro-2H-1,4-benzoxazine, fumarate.

1.1. N-(2-Hydroxyphenyl)trifluoroacetamide.

104 g (0.95 mol) of 2-aminophenol are suspended in 1.5 litres of ether in a 4 liter reactor with magnetic stirrer, and 77 ml of pyridine are added thereto. The reaction medium is cooled by a mixture of ice and ethanol. 200 g (0.95 mol) of trifluoroacetic anhydride are added dropwise in the course of 1 hour. The mixture is allowed to return to room temperature and then stirring is continued for 1 hour. Ice-water is added to the reaction medium, the aqueous phase is poured off, and the organic phase is washed in succession with 1 liter of 1N hydrochloric acid, with water, with saturated sodium hydrogen carbonate solution and then with saturated sodium chloride solution. The washed organic phase is dried over magnesium sulphate and evaporated to dryness. 170 g of product are obtained, which is used as it is in the following step.

1.2. Ethyl (±)-3,4-dihydro-2H-1,4-benzoxazine-3-acetate.

164 g (0.8 mol) of the compound obtained in 1.1 in solution in 2 liters of ethanol are placed in a 4 liter reactor with magnetic stirrer. 151 ml of a 5.3N solution of sodium methoxide and 154.43 g (0.8 mol) of ethyl 4-bromobut-2-enoate are added in succession. The mixture is heated at 80° C. for 1 hour. It is evaporated to dryness and the residue is taken up in 500 ml of water and 200 ml of 1N sodium hydroxide solution and then extracted with ether. The organic phase is washed with saturated sodium chloride solution, dried over magnesium sulphate and evaporated to dryness. 153 g of product are recovered which is purified by chromatography on a silica gel column, eluting with dichloromethane. 55 g of product are obtained.

1.3. (±)-3,4-Dihydro-2H-1,4-benzoxazine-3-ethanol.

300 ml of tetrahydrofuran are placed in a 2 liter reactor and cooled with a mixture of ice and salt. Under a stream of argon, 15 g of lithium aluminium hydride are added and then 55 g (0.25 mol) of the compound obtained in 1.2 in solution in 300 ml of tetrahydrofuran are added dropwise. The mixture is left with stirring for 2 hours. The reactor is cooled with a mixture of dry ice and acetone, and then 50 ml of water and 20 ml of 1N sodium hydroxide solution are added dropwise. The mixture is left with stirring for 2 hours and left to stand overnight. The precipitate is filtered on kieselguhr, it is rinsed in succession with tetrahydrofuran and ethyl acetate, and is concentrated to dryness. 40 g of crude product are isolated, which is purified by chromatography on a silica gel column, eluting with a 50:50 mixture of hexane/ethyl acetate. 35 g of product are obtained.

1.4. (±)-4-[3-(Trifluoromethyl)benzoyl]-3,4-dihydro-2H-1,4-benzoxazine-3-ethanol.

25 ml of dichloromethane, 8.96 g (0.08 mol) of the compound obtained in 1.3 and 7.6 g (0.055 mol) of potassium carbonate are placed in a 100 ml round-bottom flask and 8.3 ml (0.055 mol) of 3-(trifluoromethyl)benzoyl chloride in solution in 25 ml of dichloromethane are added dropwise. The mixture is left at room temperature with magnetic stirring for 2 hours. The organic phase is recovered and washed in succession with 1N sodium hydroxide solution, with water and with saturated sodium chloride solution. It is dried over magnesium sulphate and concentrated to dryness. The oil obtained is purified by chromatography on a silica gel column, eluting with a 50:50 mixture of hexane/ethyl acetate. 11 g of yellow oil are isolated, which crystallizes after standing overnight. 2 g of this oil are purified by chromatography on a silica gel column, eluting with a 3:2 mixture of hexane/ethyl acetate. 1.3 g of product are obtained.

1.5. (±)-3-(2-Chloroethyl)-4-[3-(trifluoromethyl)benzoyl]-3,4-dihydro-2H-1,4-benzoxazine.

2.9 ml of thionyl chloride are added to 3.51 g (0.01 mol) of the compound obtained in 1.4 in solution in 50 ml of dichloromethane, and the mixture is left with stirring at room temperature for 3 hours. 2.9 ml of thionyl chloride are again added and the mixture is left with stirring at room temperature for 2 hours. It is concentrated to dryness, the residue is taken up in toluene, and the mixture is concentrated again to dryness. 3.2 g of product are obtained.

1.6. 3,4-Dimethoxyphenylacetyl chloride.

103.7 ml (1.42 mol) of thionyl chloride are added to 95 g (0.48 mol) of 3,4-dimethoxyphenylacetic acid in solution in 200 ml of dichloromethane. The mixture is left with stirring for 18 hours. The solvents are evaporated. 1.4 g of crude product are isolated in the form of a brownish oil.

1.7. N-(2,2-Dimethoxyethyl)-3,4-dimethoxyphenylacetamide.

104 g (0.48 mol) of the compound obtained in 1.6, in solution in 250 ml of dichloromethane, are added dropwise to a solution of 52.7 ml (0.48 mol) of 2,2-dimethoxyethanamine, cooled at 10° C. and containing 67.5 ml of triethylamine, in 500 ml of dichloromethane. When the addition is concluded, the mixture is allowed to return to room temperature and left with stirring for 1 hour. 500 ml of ice-water are added, and the organic phase is poured off. It is recovered, washed with saturated magnesium sulphate solution and concentrated to dryness. 128 g of product are obtained in the form of a viscous oil.

1.8. 7,8-Dimethoxy-1,3-dihydro-2H-3-benzazepin-2-one.

128 g (0.45 mol) of the compound obtained in 1.7, in solution in a mixture of 640 ml of concentrated hydrochloric acid and 640 ml of acetic acid, are left with stirring at room temperature for 8 hours. The mixture is left with stirring at room temperature for 3 days. 2 kg of ice are added and the product obtained, which has precipitated in the medium, is isolated by filtration and rinsed with a mixture of water/methanol, and dried in the oven. 42 g of product are obtained. Melting point: 240°–244° C.

1.9. 7,8-Dimethoxy-1,3,4,5-tetrahydro-2H-3-benzazepin-2-one.

The compound obtained in 1.8 is hydrogenated in the presence of 1 g of 10% palladium on carbon under a pressure of 0.42 MPa at 50° C. for 3 hours. The product is concentrated to dryness, filtered on kieselguhr and rinsed with acetic acid. The residue is taken up in dichloromethane and washed in succession with saturated sodium hydrogen carbonate solution and then with water. It is dried over magnesium sulphate and concentrated to dryness. 13.2 g of product are obtained. Melting point: 186°–190° C.

1.10. 7,8-Dimethoxy-1,3,4,5-tetrahydro-2H-3-benzazepine, hydrochloride.

20 ml of a 1M solution of diborane in tetrahydrofuran are added dropwise at room temperature under argon to a suspension of 2.2 g (0.01 mol) of the compound obtained in 1.9, in solution in 25 ml of dried tetrahydrofuran. The mixture is heated at the reflux temperature for 2 hours. It is cooled with a mixture of ice and alcohol and 30 ml of 6N hydrochloric acid are added dropwise. The mixture is heated at 80° C. for 1 hour. It is rendered alkaline with 4N sodium hydroxide solution and extracted with ethyl acetate. The organic phase is recovered and washed with saturated sodium chloride solution, dried over magnesium sulphate and concentrated to dryness. The residue is taken up in 100 ml of 2-propanol containing 0.1N hydrochloric acid and the precipitate formed is isolated by filtration. It is dried, and 1 g of product is obtained. Melting point: 236° C.

1.11. (±)-3-[2-(7,8-dimethoxy-2,3,4,5-tetrahydro-1H-3-benzazepin-3-yl)ethyl]-4- [3-(trifluoromethyl)benzoyl]-3,4-dihydro-2H-1,4-benzoxazine, fumarate.

3 g (0.015 mol) of the compound obtained in 1.5 are mixed with 3.56 g (0.0096 mol) of the compound obtained in 1.10, 2.66 g of potassium carbonate, 100 mg of potassium iodide and 50 ml of dimethylformamide. The mixture is heated at 80° C. for 4 hours and then discharged into a mixture of ice and water. It is extracted with ether, and the organic phase is washed with saturated sodium chloride solution, dried over magnesium sulphate and concentrated to dryness. The residual oil is purified by chromatography on a silica gel column, eluting with a 99:1 mixture of dichloromethane/methanol and then with a 98:2 mixture of dichloromethane/methanol. 1.8 g of base are obtained. The fumarate is prepared by adding one equivalent of fumaric acid. It is isolated and recrystallized from 2-propanol. Melting point: 182°–184° C.

EXAMPLE 2

(Compound No. 16)

(±)-3-[2-(6,7-Dimethoxy-1,2,3,4-tetrahydro-2-isoquinolyl)ethyl]-4-[(4-methylphenyl)sulphonyl]-3,4-dihydro-2H-1,4-benzoxazine, oxalate.

2.1. N-(2-Hydroxyphenyl)-4-methylbenzenesulphonamide.

35 g (0.18 mol) of tosyl chloride and 60 ml of pyridine are added to 20 g (0.18 mol) of 2-aminophenol. The mixture is left with stirring at room temperature overnight. Water is added, and the mixture is extracted twice with ether. The organic phases are washed in succession with water, 1N hydrochloric acid and twice again with water. The combined phases are dried over magnesium sulphate and concentrated to dryness. 44 g of product are obtained.

2.2. Ethyl (±)-4-[(4-methylphenyl)sulphonyl]-3,4-dihydro-2H-1,4-benzoxazine-3-acetate.

5.1 g (0.03 mol) of ethyl 4-bromobut-2-enoate, 3.8 ml of a 5.3N sodium methoxide solution and 25 ml of ethanol are added to 5.3 g (0.02 mol) of the compound obtained in 2.1. The mixture is heated at the reflux temperature overnight. It is evaporated to dryness, and the residue is taken up in succession in ethyl acetate, water and, finally, in 1N sodium hydroxide solution. The organic phase is recovered and extracted, and the extract is washed with water and then with saturated sodium chloride solution. It is dried over magnesium sulphate and then evaporated to dryness. 8 g of product are obtained, which is utilized as it is in the following step.

2.3. (±)-4-[(4-Methylphenyl)sulphonyl]-3,4-dihydro-2H-1,4-benzoxazine-3-ethanol.

0.23 g (0.006 mol) of lithium aluminium hydride is dissolved under argon in 20 ml of tetrahydrofuran. 1.5 g (0.004 mol) of the compound obtained in 2.2, in solution in 5 ml of tetrahydrofuran, are added dropwise. When the reaction has finished, 0.7 g of water, 0.3 g of 1N sodium hydroxide solution and again 0.7 g of water are added in succession. The mixture is filtered over kieselguhr, the filter residue is washed with tetrahydrofuran, and the liquid is evaporated. The residue is taken up in ethyl acetate and the organic phase is washed with water. It is dried and evaporated to dryness. 1.4 g of product are obtained.

2.4. (±)-3-(2-Chloroethyl)-4-[(4-methylphenyl)-sulphonyl]-3,4-dihydro-2H-1,4-benzoxazine.

2 g (0.006 mol) of the alcohol obtained in 2.3 are dissolved in 15 ml of chloroform. 2.2 g (0.018 mol) of thionyl chloride and one drop of dimethylformamide are added dropwise. The mixture is heated at the reflux temperature for 5 hours. It is evaporated to dryness, the residue is taken up in the minimum volume of toluene, and the solution is again evaporated to dryness. 2.1 g of product are obtained.

2.5. (±)-3-[2-(6,7-Dimethoxy-1,2,3,4-tetrahydro-2-isoquinolyl)ethyl]-4-[(4-methylphenyl)sulphonyl]-3,4-dihydro-2H-1,4-benzoxazine, oxalate.

0.65 g (0.0034 mol) of 6,7-dimethoxy-1,2,3,4-tetrahydroisoquinoline and 6 ml of 3-methylbutanol are added to 1.2 g (0.0034 mol) of the compound obtained in 2.4. The mixture is heated at 80° C. overnight and evaporated to dryness. The residue is taken up in dilute ammonia and extracted twice with ether. The ethereal phases are washed with water, dried over magnesium sulphate and evaporated to dryness. The product obtained is purified by chromatography on a silica gel column, eluting with a 1% methanol/dichloromethane mixture. 0.8 g of product is obtained. The oxalate is prepared by adding one equivalent of oxalic acid. It is recrystallized from a mixture of ethyl acetate/ethanol. 0.6 g of oxalate is obtained. Melting point: 190°–192° C.

EXAMPLE 3

(Compound No. 18)

(±) -3-[2-(6,7-Dimethoxy-1,2,3,4-tetrahydroiso-2-quinolyl)ethyl]- 4-[3-(trifluoromethyl)benzoyl]-3,4-dihydro-2H-1,4-benzoxazine, oxalate.

3.1. (±)-3-[2-(6,7-Dimethoxy-1,2,3,4-tetrahydroiso-2-quinolyl)ethyl]-4-[3-(trifluoromethyl)benzoyl]-3,4-dihydro-2H-1,4-benzoxazine, oxalate.

1.24 g (0.005 mol) of the hydrochloride of 6,7-dimethoxy-1,2,3,4-tetrahydroisoquinoline, 4 g of potassium carbonate and 0.9 g of potassium iodide are added at room temperature, with stirring and under an argon atmosphere to a solution of 2.0 g (0.005 mol) of the compound obtained in 1.5, in solution in 10 ml of dimethylformamide. The mixture is heated at 80° C. for 4 hours. It is cooled, and 40 ml of water and 100 ml of ether are added. The phases are separated and the aqueous phase is extracted with twice 100 ml of ether. The organic phases are combined, washed with 100 ml of saturated sodium chloride solution, dried over magnesium sulphate, filtered and evaporated to dryness. 3 g of product are obtained in the form of a brown oil which is purified by chromatography on a silica gel column, eluting with a 1:9 mixture of methanol/dichloromethane. 1.89 g of base are obtained in the form of a yellow oil. The oxalate is prepared by adding one equivalent of oxalic acid. It is isolated and recrystallized in the form of white crystals from a mixture of isopropanol/isopropyl ether. Melting point: 126°–128° C.

EXAMPLE 4

(Compound No. 18a)

(+)-3-[2-(6,7-Dimethoxy-1,2,3,4-tetrahydroiso-2-quinolyl)ethyl]-4-[3-(trifluoromethyl)benzoyl]-3,4-dihydro-2H-1,4-benzoxazine, oxalate.

4.1. (+)-4-[3-(Trifluoromethyl)benzoyl]-3,4-dihydro-2H-1,4-benzoxazine-3-ethanol.

8.7 g (0.025 mol) of the racemic alcohol obtained in 1.4 are suspended in 1.09 liters of hexane. 7.6 ml (0.082 mol) of vinyl acetate and 4.35 g of lipase from *Mucor miehei* are added. The mixture is left for 15 hours at room temperature and filtered under vacuum. 10.7 g of yellow oil are obtained, which contains a mixture of dextrorotatory alcohol and laevorotatory acetate. They are separated by chromatography on a silica gel column, eluting with a 1:1 mixture of ethyl acetate/cyclohexane. 3.62 g of chemically pure, dextrorotatory alcohol are obtained. Optical rotation: $[\alpha]_D^{20} = +62°$ (c=0.99; dichloromethane) Enantiomeric excess: ee=99.7% (chiral HPLC).

4.2. (+)-3-(2-Chloroethyl)-4-[3-(trifluoromethyl)benzoyl]-3,4-dihydro-2H-1,4-benzoxazine.

3 ml (0.041 mol) of thionyl chloride are added at room temperature, with stirring and under an argon atmosphere to a solution of 4 g (0.011 mol) of the alcohol obtained in 4.1, in 20 ml of dichloromethane. Stirring is continued at room temperature for 18 hours. The mixture is evaporated to dryness and the product obtained is utilized as it is in the following step. 4.46 g of product are obtained.

4.3. (+)-3-[2-(6,7-Dimethoxy-1,2,3,4-tetrahydro-2-isoquinolyl)ethyl]-4-[3-(trifluoromethyl)benzoyl]-3,4-dihydro-2H-1,4-benzoxazine, oxalate.

2.31 g (0.012 mol) of the hydrochloride of 6,7-dimethoxy-1,2,3,4-tetrahydroisoquinoline and 3.31 g (0.024 mol) of potassium carbonate are added at room temperature, with stirring and under an argon atmosphere to a solution of 4.46 g (0.012 mol) of the compound obtained in 4.2, in 40 ml of dimethylformamide. The mixture is heated for 4 hours at 80° C. and then cooled. 40 ml of water and 100 ml of ether are added in succession, the phases are separated, and the aqueous phase is extracted with twice 100 ml of ether. The organic phases are combined and washed with 100 ml of saturated sodium chloride solution. They are dried over magnesium sulphate, filtered and evaporated to dryness. 7 g of product are obtained, which is purified by chromatography on a silica gel column, eluting with a 1:9 mixture of methanol/dichloromethane. 1.17 g of base are obtained in the form of an oil. The oxalate is prepared by adding one equivalent of oxalic acid. It is isolated and recrystallized, in the form of white crystals, from a mixture of ethyl acetate, isopropyl ether and acetone. Melting point: 128°–129° C. Optical rotation: $[\alpha]_D^{20} = +69°$ (c=0 976; methanol)

EXAMPLE 5

(Compound No. 18b)

(−)-3-[2-(6,7-Dimethoxy-1,2,3,4-tetrahydro-2-isoquinolyl)ethyl]- 4-[3-(trifluoromethyl)benzoyl]-3,4-dihydro-2H-1,4-benzoxazine, oxalate.

5.1. (−)-4-[3-(Trifluoromethyl)benzoyl]-3,4-dihydro-2H-1,4-benzoxazine-3-ethanol.

8.7 g (0.025 mol) of the racemic alcohol obtained in 1.4 are suspended in 1.09 liters of hexane. 7.6 ml (0.082 mol) of vinyl acetate and 4.35 g of lipase from Mucor miehei are added. The mixture is left for 15 hours at room temperature and filtered under vacuum. 10.7 g of yellow oil are obtained, which contains a mixture of dextrorotatory alcohol and laevorotatory acetate. They are separated by chromatography on a silica gel column, eluting with a 1:1 mixture of ethyl acetate/cyclohexane.

6.14 g of laevorotatory acetate (ee=70%) are obtained in the form of an oil which is triturated in 200 ml of hexane. A precipitate is obtained corresponding to the racemic acetate, which is filtered off. The filtrate is evaporated to dryness. 3.94 g of chemically pure, laevorotatory acetate are obtained. Optical rotation: $[\alpha]_D^{20} = -43°$ (c=1.2; dichloromethane) Enantiomeric excess: ee=99.5% (chiral HPLC).

3.94 g of laevorotatory acetate are dissolved in 40 ml of toluene. 200 ml of 0.01M phosphate buffer ($KH_2PO_4$/$Na_2PO_4$), pH 7.2, and 1.2 g of lipase from Mucor miehei are added. The mixture is stirred overnight at room temperature, maintaining a constant pH by addition of 0.5M aqueous sodium hydroxide solution, using a pH-stat. 100 ml of ethyl ether are added, the organic phase is separated off, and the aqueous phase is extracted with twice 100 ml of ether. The organic phases are combined and washed with saturated sodium chloride solution. They are dried over magnesium sulphate, filtered and evaporated to dryness. 2.8 g of chemically pure, laevorotatory alcohol are obtained. Optical rotation: $[\alpha]_D^{20} = -59.8°$ (c=1.32; dichloromethane) Enantiomeric excess: ee=96.5% (chiral HPLC).

5.2. (−)-3-(2-chloroethyl)-4-[3-(trifluoromethyl)benzoyl]-3,4-dihydro-2H-1,4-benzoxazine.

3 ml (0.041 mol) of thionyl chloride are added at room temperature, with stirring and under an argon atmosphere to a solution of 2.8 g (0.080 mol) of the alcohol obtained in 5.1, in 20 ml of dichloromethane. Stirring is continued at room temperature for 18 hours. The mixture is evaporated to dryness and the product obtained is used as it is in the following step. 3.04 g of product are obtained.

5.3. (−)-3-[2-(6,7-Dimethoxy-1,2,3,4-tetrahydro-2-isoquinolyl)ethyl]-4-[3-(trifluoromethyl)benzoyl]-3,4-dihydro-2H-1,4-benzoxazine, oxalate.

3.17 g (0.016 mol) of the hydrochloride of 6,7-dimethoxy-1,2,3,4-tetrohydroisoquinoline and 2.26 g (0.016 mol) of potassium carbonate are added at room temperature, with stirring and under an argon atmosphere to a solution of 3.04 g (0.008 mol) of the compound obtained in 5.2, in 40 ml of dimethylformamide. The mixture is heated at 80° C. for 4 hours and then cooled. 40 ml of water and 100 ml of ether are added in succession, the phases are separated, and the aqueous phase is extracted with twice 100 ml of ether. The organic phases are combined and washed with 100 ml of saturated sodium chloride solution. They are dried over magnesium sulphate, filtered and evaporated to dryness. 5 g of product are obtained, which is purified by chromatography on a silica gel column, eluting with a 1:9 mixture of methanol/dichloromethane. 1.30 g of base are obtained in the form of an oil. The oxalate is prepared by adding one equivalent of oxalic acid. It is isolated and recrystallized, in the form of white crystals, from a mixture of 2-propanol, diisopropyl ether and acetone. Melting point: 129°–130° C. Optical rotation: $[\alpha]_D^{20} = -71°$ (c=1.03; methanol).

EXAMPLE 6

(Compound No. 38)

(±)-3-[2-(6,7-dimethoxy-1,2,3,4-tetrahydro-2-isoquinolyl)ethyl]-6-methyl-4-[3-(trifluoromethyl)benzoyl]-3,4-dihydro-2H-1,4-benzoxazine, oxalate.

6.1. N-(2-Hydroxy-5-methylphenyl)trifluoroacetamide.

A suspension is prepared from 350 ml of diethyl ether and 25 g (0.2 mol) of 2-amino-4-methylphenol in a 1 liter reactor with magnetic stirrer, 20.5 ml of pyridine are added, the reaction medium is cooled with a mixture of ice and ethanol, and 28 ml (0.2 mol) of trifluoroacetic anhydride are added dropwise in the course of one hour. The mixture is allowed to return to room temperature and stirring is maintained for 2 hours.

Ice-water is added, the organic phase is separated, washed in succession with 1N hydrochloric acid, with water, with saturated sodium hydrogen carbonate solution and with saturated sodium chloride solution and dried over magnesium sulphate, and the solvent is evaporated. 37.07 g of product are obtained, which is used as it is in the following step.

6.2. Ethyl (±)-6-methyl-3,4-dihydro-2H-1,4-benzoxazine-3-acetate.

In a 3 liter reactor with magnetic stirrer, cooled to 0° C., 760 ml of ethanol are introduced and slowly, in small portions, 5.79 g (0.252 mol) of sodium are added and then, dropwise, 37.45 g (0.17 mol) of N-(2-hydroxy-5-methylphenyl)trifluoroacetamide and 43.7 g (0.17 mol) of 75% pure ethyl 4-bromobut-2-enoate, and the mixture is heated at 110° C. for 2 hours.

The solvent is evaporated, and the residue is taken up in 100 ml of water and 40 ml of 1N sodium hydroxide solution and extracted with diethyl ether. The organic phase is washed with saturated sodium chloride solution, and dried over magnesium sulphate, and the solvent is evaporated. 28.58 g of product are obtained, which is purified by chromatography on a silica gel column, eluting with a 50:50 mixture of cyclohexane/isopropyl ether. 23.48 g of product are obtained.

6.3. (±)-6-Methyl-3,4-dihydro-2H-1,4-benzoxazine-3-ethanol.

150 ml of tetrahydrofuran are placed in a 1 liter reactor and cooled with a mixture of ice and salt, and, under an argon atmosphere, 6 g (0.158 mol) of lithium aluminium hydride are added and then, dropwise, 23.48 g (0.099 mol) of ethyl (±)-6-methyl-3,4-dihydro-2H-1,4-benzoxazine-3-acetate in solution in 150 ml of tetrahydrofuran, and stirring is maintained for 1.5 hours. The reactor is cooled with a mixture of dry ice and acetone, 40 ml of water and 20 ml of 1N sodium hydroxide solution are added dropwise, and the mixture is left with stirring for 0.5 hour.

The precipitate is filtered on kieselguhr and rinsed with tetrahydrofuran and then with ethyl acetate, and the solvent is evaporated. 20.29 g of crude product are isolated, which is purified by chromatography on a silica gel column, eluting with a 50:50 mixture of cyclohexane/ethyl acetate. 22.94 g of product are obtained.

6.4. (±)-6-Methyl-4-[3-(trifluoromethyl)benzoyl]-3,4-dihydro-2H-1,4-benzoxazine-3-ethanol.

200 ml of dichloromethane, 22.87 g (0.118 mol) of 6-methyl-3,4-dihydro-2H-1,4-benzoxazine-3-ethanol and 17.53 g (0.125 mol) of potassium carbonate are placed in a 1 liter round-bottom flask, and 26.19 g (0.125 mol) of 3-(trifluoromethyl)benzoyl chloride in solution in 200 ml of dichloromethane are added dropwise, and stirring is maintained at room temperature for 3 hours. 120 ml of 1N sodium hydroxide solution are added, the organic phase is separated and washed with water and then with saturated sodium chloride solution and dried over magnesium sulphate, and the 46.25 g of oil obtained are purified by chromatography on a silica gel column, eluting with a 6:4 mixture of cyclohexane/ethyl acetate. 19.66 g of product are obtained.

6.5. (±)-3-(2-Chloroethyl)-6-methyl-4-[3-(trifluoromethyl)benzoyl]-3,4-dihydro-2H-1,4benzoxazine.

19.6 ml (0.27 mol) of thionyl chloride are added to 19.66 g (0.054 mol) of (±)-6-methyl-4-[3-(trifluoromethyl)benzoyl]-3,4-dihydro-2H-1,4-benzoxazine-3-ethanol in solution in 230 ml of dichloromethane, and the mixture is stirred at room temperature for 4 hours. The solvent and the excess thionyl chloride are evaporated, the residue is taken up in toluene, which is evaporated, and the residue is purified by chromatography on a silica gel column, eluting with a 2:1 mixture of cyclohexane/isopropyl ether.

13.83 g of product are obtained.

6.6. (±)-3-[2-(6,7-Dimethoxy-1,2,3,4-tetrahydro-2-isoquinolyl)ethyl]-6-methyl-4-[3-(trifluoromethyl)benzoyl]-3,4-dihydro-2H-1,4-benzoxazine, oxalate.

1.19 g (0.005 mol) of the hydrochloride of 6,7-dimethoxy-1,2,3,4-tetrahydroisoquinoline, 1.78 g (0.013 mol) of potassium carbonate and 0.82 g (0.005 mol) of potassium iodide are added at room temperature, under an argon atmosphere and with magnetic stirring to a solution of 2 g (0.005 mol) of (±)-3-(2-chloroethyl)-6-methyl-4-[3-(trifluoromethyl)benzoyl]-3,4-dihydro-2H-1,4-benzoxazine in 20 ml of N,N-dimethylformamide, and the mixture is heated at 150° C. for 1 hour.

It is cooled, 55 ml of water and 50 ml of diethyl ether are added, the phases are separated, the aqueous phase is extracted with twice 50 ml of diethyl ether, the organic phases are combined, washed with 100 ml of saturated sodium chloride solution, dried over magnesium sulphate and filtered, and the solvent is evaporated. 3.75 g of product are obtained in the form of an oil, which is purified by chromatography on a silica gel column, eluting with a 95:5 mixture of dichloromethane/methanol. 0.450 g of pure base is obtained in the form of a yellow oil. The oxalate is prepared by adding one equivalent of oxalic acid, which is isolated and recrystallized, in the form of white crystals, from 2-propanol. 0.180 g of oxalate (acid:base ratio=0.8:1) are obtained. Melting point: 164°–166° C.

EXAMPLE 7

(Compound No. 35)

(±)-6-Chloro-3-[2-(2,3,4,5-tetrahydro-1H-3-benzazepin-3-yl)ethyl]-4-[3-(trifluoromethyl)benzoyl]-3,4-dihydro-2H-1,4-benzoxazine, oxalate.

7.1. N-(5-Chloro-2-hydroxyphenyl)trifluoroacetamide.

25 g (0.174 mol) of 2-amino-4-chlorophenol are suspended in 320 ml of diethyl ether in a 1 liter reactor with magnetic stirrer, 18 ml of pyridine are added, the medium is cooled with a mixture of ice and ethanol, 24.6 ml (0.174 mol) of trifluoroacetic anhydride are added dropwise in the course of 1 hour, the mixture is allowed to return to room temperature, and stirring is continued for 1 hour. Ice-water is added, the phases are separated, the organic phase is washed in succession with 320 ml of 1N hydrochloric acid, with water, with saturated sodium hydrogen carbonate solution and then saturated sodium chloride solution and dried over magnesium sulphate, and the solvent is evaporated. 40.3 g of product are obtained, which is used as it is in the following step.

7.2. Ethyl (±)-6-chloro-3,4-dihydro-2H-1,4-benzoxazine-3-acetate.

420 ml of ethanol are introduced into a 3 liter reactor with magnetic stirrer, cooled to 0° C., 3.8 g (0.166 mol) of sodium are added slowly in small portions and then, in succession and dropwise, 40 g (0.166 mol) of N-(5-chloro-2-hydroxyphenyl)trifluoroacetamide and 40 g (0.155 mol) of 75% pure ethyl 4-bromobut-2-enoate are added, and the mixture is heated at 85° C. for 2 hours. The solvent is evaporated and the residue is taken up in 100 ml of water and 40 ml of 1N sodium hydroxide solution and extracted with diethyl ether. The organic phase is separated off, washed with saturated aqueous sodium chloride solution, dried over magnesium sulphate and evaporated. 28.58 g of product are obtained, which is purified by chromatography on a silica gel column, eluting with a 50:50 mixture of cyclohexane/isopropyl ether. 23.72 g of product are obtained.

7.3. (±)-6-Chloro-3,4-dihydro-2H-1,4-benzoxazine-3-ethanol.

150 ml of tetrahydrofuran are placed in a 1 liter reactor which is cooled with a mixture of ice and salt and, under an argon atmosphere, 5.92 g (0.156 mol) of lithium aluminium hydride are added and then, dropwise, 23.52 g (0.0973 mol) of ethyl (±)-6-chloro-3,4-dihydro-2H-1,4-benzoxazine-3-acetate solution in 150 ml of tetrahydrofuran, and the mixture is stirred for 1.5 hours. The reactor is cooled with a mixture of dry ice and acetone, and 40 ml of water and 20 ml of 1N sodium hydroxide solution are added dropwise, the mixture is stirred for 0.5 hour, the precipitate is filtered off on kieselguhr and rinsed with tetrahydrofuran and then with ethyl acetate, and the solvent is evaporated. 27.5 g of crude product are isolated, which is purified by chromatography on a silica gel column, eluting with a 50:50 mixture of cyclohexane/ethyl acetate. 19.67 g of product are obtained.

7.4. (±)-6-chloro-4-[3-(trifluoromethyl)benzoyl]-3,4-dihydro-2H-1,4-benzoxazine-3-ethanol.

100 ml of dichloromethane, 19.17 g (0.09 mol) of (±)-6-chloro-3,4-dihydro-2H-1,4-benzoxazine-3-ethanol and 13.3 g (0.096 mol) of potassium carbonate are introduced into a 1 liter round-bottom flask, and 20 g (0.096 mol) of 3-(trifluoromethyl)benzoyl chloride in solution in 100 ml of dichloromethane are added dropwise, and the mixture is stirred at room temperature for 3 hours. 90 ml of 1N sodium hydroxide solution are added, the organic phase is separated off, washed with water and then with saturated sodium chloride solution and dried over magnesium sulphate, and the solvent is evaporated. 36 g of an oily product are obtained, which is purified by chromatography on a silica gel column, eluting with a 2:1 mixture of cyclohexane/ethyl acetate. 24.21 g of product are obtained.

7.5. (±)-6-Chloro-3-(2-chloroethyl)-4-[3-(trifluoromethyl)benzoyl]-3,4-dihydro-2-H-1,4-benzoxazine.

18 ml (0.25 mol) of thionyl chloride are added to 24.21 g of (±)-6-chloro-4-[3-(trifluoromethyl)benzoyl]-3,4-dihydro-2H-1,4-benzoxazine-3-ethanol in solution in 260 ml of dichloromethane, and the mixture is stirred at room temperature for 6 hours. The solvent is evaporated, and the residue is taken up in toluene and evaporated. The 25.21 g of oil obtained are purified by chromatography on a silica gel column, eluting with a 50:50 mixture of cyclohexane/isopropyl ether. 23.73 g of product are obtained.

7.6. (±)-6-Chloro-3-[2-(2,3,4,5-tetrahydro-1H-3-benzazepin-3-yl)ethyl]-4-[3,4-dihydro-2H-1,4-benzoxazine, oxalate.

0.9 g (0.005 mol) of the hydrochloride of 2,3,4,5-tetrahydro-1,H-3-benzazepine, 1.7 g (0.0124 mol) of potassium carbonate and 0.82 g (0.005 mol) of potassium iodide are added at room temperature, with stirring and under an argon atmosphere to a solution of 2 g (0.005 mol) of (±)-6-chloro-3-(2-chloroethyl)-4-[3-(trifluoromethyl)benzoyl]-3,4-dihydro-2H-benzoxazine in 20 ml of N,N dimethylformamide, and the mixture is heated at 110° C. for 1 hour. It is cooled, 55 ml of water and 50 ml of diethyl ether are added, the phases are separated, and the aqueous phase is extracted with twice 50 ml of diethyl ether. The organic phases are combined, washed with 100 ml of saturated sodium chloride solution, dried over magnesium sulphate and filtered, and the solvent is evaporated. 2.5 g of product are obtained in the form of an oil which is purified by chromatography on a silica gel column, eluting with a 98:2 mixture of dichloromethane/methanol. 1.84 g of pure base are obtained in the form of a yellow oil, from which the oxalate is prepared by adding one equivalent of oxalic acid and recrystallizing the product from ethanol. Melting point: 192°-194° C.

The table on the following page illustrates the chemical structures and the physical properties of some compounds according to the invention.

Legend to the table:
  in column "R₁", "n-A-C₆H₄" represents a phenyl group substituted in position n of the ring with a group A;
  in the column "Salt", "-" designates a compound in base form, "ox." designates an oxalate and "fum." designates a fumarate; when the molar ratio of acid:base is different from 1:1 it is indicated in brackets;
  in the column "m.p. (°C.)", "dec" signifies "melting with decomposition".

TABLE

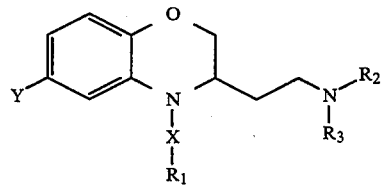

(I)

| No. | R₁ | X | Y | NR₂R₃ | Salt | m.p. (°C.) |
|---|---|---|---|---|---|---|
| 1 | 4-F—C₆H₄— | CO | H | (N,N-dimethyl-3,4-dimethoxyphenethylamine) | ox. | 164–166 |
| 2 | 4-CH₃—C₆H₄— | SO₂ | H | —N(CH₃)—(CH₂)₃CH₃ | ox. | 79–81 |
| 3 | 3-CF₃—C₆H₄— | CO | H | —N(CH₃)—(CH₂)₃CH₃ | ox. | 151–152 |
| 4 | 3-CF₃—C₆H₄ | CO | H | (N-methyl-N-benzylamine) | ox. | 108–110 (dec) |
| 5 | 3-CF₃—C₆H₄ | CO | H | (N-methyl-N-phenethylamine) | ox. | 175–176 |
| 6 | 4-CH₃—C₆H₄ | SO₂ | H | (N-methyl-N-phenethylamine) | ox. | 124–126 |
| 7 | 3-CF₃—C₆H₄ | CO | H | (N-methyl-N-(3,4-dimethoxyphenethyl)amine) | ox. | 143–144 |
| 8 | 4-CF₃—C₆H₄ | CO | H | (N-methyl-N-(3,4-dimethoxyphenethyl)amine) | ox. | 134–136 |
| 9 | 4-CH₃—C₆H₄ | SO₂ | H | (N-methyl-N-(3,4-dimethoxyphenethyl)amine) | ox. | 104–106 |

TABLE-continued (I)

Structure: Y-substituted phenyl ring with O-CH2-CH(-CH2-N(R2)(R3))-N(X-R1)

| No. | R1 | X | Y | NR2R3 | Salt | m.p. (°C.) |
|---|---|---|---|---|---|---|
| 10 | 3-CF3—C6H4 | CO | H | 3,4,5-trimethoxyphenethyl-N(CH3)- (N,N-dimethyl-2-(3,4,5-trimethoxyphenyl)ethylamine) | ox. | 95 (dec) |
| 11 | 3-CF3—C6H4 | CO | H | N,N-dimethyl-2-(2-pyridyl)ethylamine | ox. (2:1) | 105–106 |
| 12 | 4-CH3—C6H4 | SO2 | H | N,N-dimethyl-2-(2-pyridyl)ethylamine | ox. (2:1) | 148–150 |
| 13 | 4-C6H5—C6H4 | CO | H | N,N-dimethyl-2-(3,4-dimethoxyphenyl)ethylamine | ox. | 150 |
| 14 | 2-thienyl | CO | H | N,N-dimethyl-2-(3,4-dimethoxyphenyl)ethylamine | ox. | 174–176 |
| 15 | 4-CH3—C6H4 | CO | H | 6,7-dimethoxy-1,2,3,4-tetrahydroisoquinolin-2-yl | — | 181–183 |
| 16 | 4-CH3—C6H4 | SO2 | H | 6,7-dimethoxy-1,2,3,4-tetrahydroisoquinolin-2-yl | ox. | 190–192 |
| 17 | 3-CF3—C6H4 | CO | H | 6-methoxy-1,2,3,4-tetrahydroisoquinolin-2-yl | fum. | 166–168 |
| 18 (±) | 3-CF3—C6H4 | CO | H | 6,7-dimethoxy-1,2,3,4-tetrahydroisoquinolin-2-yl | ox. | 126–128 |
| 18a (+) | $[\alpha]_D^{20} = +69°$ | | | (c = 0.98; methanol) | ox | 128–129 |
| 18b (−) | $[\alpha]_D^{20} = -71°$ | | | (c = 1.03; methanol) | ox | 129–130 |

TABLE-continued
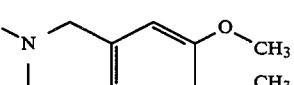
| No. | R₁ | X | Y | NR₂R₃ | Salt | m.p. (°C.) |
|---|---|---|---|---|---|---|
| 19 | 4-CF₃—C₆H₄ | CO | H | 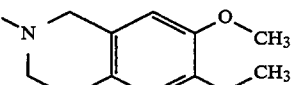 | fum. (1.5:1) | 202–205 |
| 20 | 4-OCH₃—C₆H₄ | CO | H | 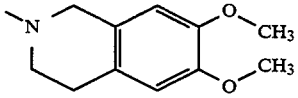 | — | 162 |
| 21 | 4-C₆H₅—C₆H₄ | CO | H | 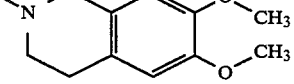 | — | 161–162 |
| 22 | 2-thienyl | CO | H | 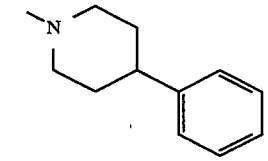 | fum. | 178–180 |
| 23 | 4-CH₃—C₆H₄ | SO₂ | H | 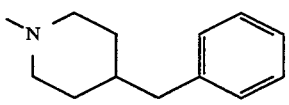 | ox. | 235–237 |
| 24 | 4-CH₃—C₆H₄ | CO | H | 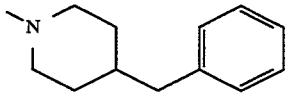 | ox. | 186–188 |
| 25 | 4-CH₃—C₆H₄ | SO₂ | H | 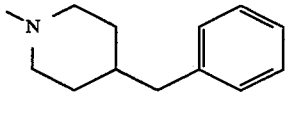 | ox. | 209–211 |
| 26 | 3-CF₃—C₆H₄ | CO | H | 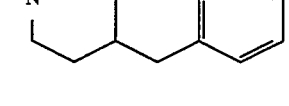 | ox. | 182–183 |
| 27 | 4-C₆H₅—C₆H₄ | CO | H | 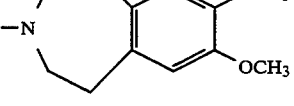 | fum. | 220–223 |
| 28 | 3-CF₃—C₆H₄ | CO | H | | fum. | 182–184 |

TABLE-continued (I) Structure: phenyl ring with O at top connecting to a chain -CH2-CH(NR2R3 side via CH2CH2)-N(X-R1)- ring Y substituent

| No. | R₁ | X | Y | NR₂R₃ | Salt | m.p. (°C.) |
|---|---|---|---|---|---|---|
| 29 | 3-CF₃—C₆H₄ | CO | H | 2,3,4,5-tetrahydro-1H-3-benzazepin-3-yl | — | 185–186 |
| 30 | 3-CF₃—C₆H₄ | CO | H | 5,8-dimethoxy-2-methyl-1,2,3,4-tetrahydroisoquinolin-2-yl | — | 125–126 |
| 31 | 3-CF₃—C₆H₄ | CO | F | 1,2,3,4-tetrahydroisoquinolin-2-yl | ox. (1.1:1) | 115–116 |
| 32 | 3-CF₃—C₆H₄ | CO | F | 5,8-dimethoxy-1,2,3,4-tetrahydroisoquinolin-2-yl | — | 142–143 |
| 33 | 3-CF₃—C₆H₄ | CO | F | 6,7-dimethoxy-1,2,3,4-tetrahydroisoquinolin-2-yl | fum. (0.5:1) | 119–120 |
| 34 | 3-CF₃—C₆H₄ | CO | Cl | 6,7-dimethoxy-1,2,3,4-tetrahydroisoquinolin-2-yl | ox. (1.6:1) | 123–125 |
| 35 | 3-CF₃—C₆H₄ | CO | Cl | 2,3,4,5-tetrahydro-1H-3-benzazepin-3-yl | ox. | 192–194 |
| 36 | 3-CF₃—C₆H₄ | CO | CH₃ | 1,2,3,4-tetrahydroisoquinolin-2-yl | ox. | 196–198 |
| 37 | 3-CF₃—C₆H₄ | CO | CH₃ | 5,8-dimethoxy-1,2,3,4-tetrahydroisoquinolin-2-yl | ox. (0.8:1) | 111–114 |

TABLE-continued (I)

| No. | R₁ | X | Y | NR₂R₃ | Salt | m.p. (°C.) |
|---|---|---|---|---|---|---|
| 38 | 3-CF₃—C₆H₄ | CO | CH₃ | 6,7-dimethoxy-1,2,3,4-tetrahydroisoquinolinyl | ox. (0.8:1) | 164–166 |
| 39 | 3-CF₃—C₆H₄ | CO | CH₃ | 2,3,4,5-tetrahydro-1H-2-benzazepinyl | — | 139–141 |
| 40 | 3-CF₃—C₆H₄ | CO | OCH₃ | 1,2,3,4-tetrahydroisoquinolinyl | ox. | 149–151 |
| 41 | 3-CF₃—C₆H₄ | CO | OCH₃ | 5,8-dimethoxy-1,2,3,4-tetrahydroisoquinolinyl | ox. | 167–169 |
| 42 | 3-CF₃—C₆H₄ | CO | OCH₃ | 6,7-dimethoxy-1,2,3,4-tetrahydroisoquinolinyl | ox. | 172–174 |

The compounds of the invention have been the subject of pharmacological tests which have demonstrated their relevance as active substances in therapy.

Inhibition of the intake of calcium induced by KCl in sections from the cortex of the immature rat 8 day old male or female Sprague-Dawley rats are used. After cervical dislocation the brain is excised and sections from the parietal cortex are prepared.

The intracellular calcium concentration ($[Ca^{2+}]_i$) is measured according to the technique described in *J. Pharm. Exp. Ther.* (1992) 261 324–330. The sections thus taken are incubated at 24° C. for 75 minutes in Krebs buffer which is saturated with $O_2/CO_2$ (95%/5%) and contains Fura-2 AM ™ at a concentration of 7 µM. After incubation the sections are rinsed a number of times with the same buffer and are left in this buffer until they are used. To measure the $[Ca^{2+}]_i$, the sections are placed at 30° C. in the cell of a spectrofluorimeter which is perfused with Krebs buffer via a pump. The sections are depolarized by perfusing Krebs buffer containing 50 mM KCl for 3 minutes. The compound to be tested is introduced into the perfusion liquid 7 minutes after this first depolarization, and a second depolarization is carried out 7 minutes after introducing the compound to be tested. The fluorescence is followed at two excitation wavelengths: 340 nm (calcium-linked form) and 380 nm (free form), the emission wavelength being 510 nm. The $[Ca^{2+}]_i$ is calculated according to the method described in *J. Biol. Chem.* (1985) 260 3440–3450. The inhibitory effect of the compounds to be tested is calculated in relation to the increase in the $[Ca^{2+}]_i$ induced by 50 mM KCl which is taken as 100%.

The percentage inhibition of the intake of $Ca^{2+}$, which is induced by the compounds of the invention, is dose-dependent and is between 10 and 65% for concentrations of from 10 to 30 µM.

Complete cerebral ischaemia in the mouse

The compounds of the invention were subjected to the test of complete cerebral ischaemia in the mouse. The ischaemia results from cardiac arrest induced by rapid intravenous injection of magnesium chloride. In this test the "survival time" is measured, i.e. the interval between the time of injection of magnesium chloride and the last observable respiratory movement of each mouse. This last movement is taken to be the ultimate index of a function of the central nervous system.

Respiratory arrest occurs approximately 19 seconds after the injection of magnesium chloride. Male mice (SWISS OF₁ IFFA CREDO) are studied in groups of 10. Before the tests they are supplied with food and drink ad libitum. The survival time is measured 10 minutes after the intraperitoneal administration of the compounds of the invention. The results are given in the form of the difference between the survival time measured in a group of 10 mice having received the compound and the survival time measured in a group of 10 mice having received the liquid vehicle. The relationships between the differences in the survival time and the dose of the compound are recorded graphically in accordance with a semilogarithmic curve. This curve enables the calculation of the "3 second effective dose" ($DE_{3''}$), i.e. the dose (in mg/kg) which produces an increase of 3 seconds in the survival time in relation to the control group of 10 untreated mice. An increase of 3 seconds in the survival time is both statistically significant and reproducible. The $DE_{3''}$'s of the compounds of the invention range from 0.2 to 60 mg/kg by the intraperitoneal route.

Study of the potential-dependent ("voltage-dependent") barium currents by the so-called "patch-clamp" technique The barium currents passing through the potential-dependent calcium channels are measured on cultured cells (6 to 10 day cultures) from the cortex of the newborn rat (Sprague-Dawley). The measurement chambers, which have a volume of 800 μl and contain the rat cortex cells, are placed on the platform of an Olympus IMT-2 TM inverted microscope and viewed at 400× magnification. The chambers are continuously perfused (4 to 5 ml/min) using a solution-distributing device which accepts 9 inputs (dead space<50 μl) and of which the sole outlet, consisting of a polyethylene tube with an opening of 500 μm, is placed less than 3 mm from the cell being studied. This device has the advantage of permitting a rapid changeover of solution for the cells being studied.

The patch-clamp method used is described in *Pfluegers Archives* (1981) 391 85–100. An Axopatch-1D TM amplifier combined with an AT 386–33 MHz computer and using the PCLAMP TM software from Axon Instruments TM is employed for cell stimulation, data acquisition and the analysis of the results. To record the barium currents, borosilicate glass pipettes are brought close to the cells using a Narishige WR 60 TM hydraulic micromanipulator. The tip of the pipettes is filled with the intracellular reference solution, which has the following composition (in mM): CaCl (140), $CaCl_2$ (1), $Na_2ATP$ (4), EGTA (11; pCa=8), HEPES (10), Tris-OH (pH=7.2). Once the configuration of the entire cell has been obtained, the cell is perfused with a so-called TEA-barium solution which has the following composition (in mM): TEA-Cl (144), $BaCl_2$ (5), $MgCl_2$ (2), CsCl (3), glucose (10), HEPES (10), Tris-OH (pH=7.4). This solution enables the measurement of the calcium current (correlated with the barium current passing through the potential-dependent calcium channels) independently of the effect of the sodium and potassium currents. The overall potential-dependent barium current is obtained by applying a depolarizing surge in potential lasting for 250 ms and taking the membrane potential from −80 mV to −16 mV. The stimulation frequency is 0.25 Hz.

The compounds of the invention are dissolved in the TEA-barium medium and are applied once the amplitude of the barium current has stabilized. After a stable inhibitory effect has been obtained, the cell is again perfused with the TEA-barium control solution in order to observe the reversal of the effect.

The effect obtained is compared with that of a 100 μM cadmium solution. The blocking effects on the potential-dependent calcium channels vary as a function of those doses of the compounds which were studied and, for the most active compounds, are of the order of 66% at a concentration of 1 μM and 100% at a concentration of 10 μM.

The results of the tests carried out on the compounds of the invention show that, in vitro, they have neuronal calcium-antagonist properties and, in vivo, they have neuroprotective and antiischaemic properties. For this purpose an effective amount of a said compound may be administered to a subject in whom a neuroprotective or antiischaemic effect is desired.

The results suggest that the compounds can be used for the treatment and prevention of cerebral disorders such as those which follow on, for example, from an ischaemic attack, cardiac or respiratory arrest, or a cerebral embolism or thrombosis, for the treatment of cerebral senility, of the dementia following multiple infarcts, of senile dementia, for example of Alzheimer's disease or of Pick's disease, for the treatment of olivopontocerebellar atrophy and of other neurodegenerative diseases such as Huntington's chorea, amyotrophic lateral sclerosis, for the treatment of cranial or spinal trauma, for the prevention of the neuronal damage which follows convulsive states, for the treatment of certain cancers, for the treatment of the neurological alterations which result from AIDS and for the treatment of diabetic retinopathies.

In this context they can be present in any pharmaceutical form which is suitable for enteral or parenteral administration, in association with appropriate excipients, for example in the form of plain or coated tablets, hard gelatin and other capsules, suppositories, or drinkable or injectable solutions or suspensions, in doses which enable the daily administration of from 0.1 to 1000 mg of active substance.

We claim:

1. A compound, in the form of a pure optical isomer or a mixture of optical isomers, of the formula:

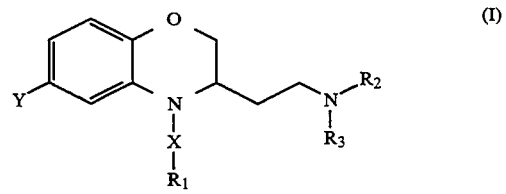

in which

Y represents hydrogen, fluorine, chlorine, methyl or methoxy, $R_1$ represents phenyl substituted by fluorine, methyl, methoxy, trifluoromethyl or phenyl, or $R_1$ represents 2-thienyl, $R_2$ represents methyl, and $R_3$ represents $(C_1-C_4)$-alkyl, phenyl-$(C_1-C_2)$-alkyl which is unsubstituted or substituted on the ring by 2 to 3 methoxy groups, or 2-(2-pyridyl)ethyl, or $R_2$ and $R_3$ together form, with the nitrogen to which they are attached, 4-phenyl(1-piperidyl), 4-phenylmethyl(1-piperidyl), 1,2,3,4-tetrahydro-2-isoquinolyl, 6-methoxy-1,2,3,4-tetrahydro-2-isoquinolyl, 5,8-dimethoxy-1,2,3,4-tetrahydro-2-isoquinolyl, 6,7-dimethoxy-1,2,3,4-tetrahydro-2-isoquinolyl, 2,3,4,5-tetrahydro-1H-3-benzazepin-3-yl, or 7,8-dimethoxy-2,3,4,5-tetrahydro-1H-3-benzazepin-3-yl, and X represents carbonyl or sulphonyl, and its addition salts with pharmaceutically acceptable acids.

2. A compound according to claim 1, wherein $R_1$ represents 3-(trifluoromethyl)phenyl, $R_2$ and $R_3$ form, with the adjacent nitrogen, 6,7-dimethoxy-1,2,3,4-tetrahydro-2-isoquinolyl, and X represents carbonyl.

3. A pharmaceutical composition, comprising a compound according to claim 1, in combination with an excipient.

4. Method of providing an antiischaemic effect in a subject which comprises administering to said subject an effective amount of a compound according to claim 1.

* * * * *